United States Patent [19]

DuCharme et al.

[11] 4,007,181
[45] Feb. 8, 1977

[54] ADAMANTYL CONTAINING GUANIDINES

[75] Inventors: Donald W. DuCharme, Copper Township, Kalamazoo County; Louis L. Skaletzky, Kalamazoo, both of Mich.

[73] Assignee: The Upjohn Company, Kalamazoo, Mich.

[22] Filed: Feb. 11, 1974

[21] Appl. No.: 441,398

[52] U.S. Cl. .................. 260/247.5 R; 260/239 B; 260/243 B; 260/268 TR; 260/293.56; 260/326.86; 260/564 D; 424/244; 424/246; 424/248.56; 424/250; 424/267; 424/274; 424/326

[51] Int. Cl.² ...................................... C07D 295/14

[58] Field of Search ............ 260/247.5 R, 268 TR, 260/239 B, , 293.56, 326.86, 564 A, 243 B

[56] References Cited

UNITED STATES PATENTS

| 3,270,054 | 8/1966 | Gagneus | 260/564 A |
|---|---|---|---|
| 3,401,201 | 9/1968 | Walton | 260/566 |
| 3,646,024 | 2/1972 | Mullins | 260/247.5 R |
| 3,838,151 | 9/1974 | Grisar | 260/239 B |

FOREIGN PATENTS OR APPLICATIONS 1,192,453  1/1966  Germany

OTHER PUBLICATIONS

Moffatt, J.A.C.S., 83, 649 (1961).
Kurzer, Chem. Rev., 67, 107 (1967).
Kurokawa, J. Neurochem, 5, 283 (1960).
Gall, Immunology, 11, 369 (1966).
Ovsepyan, Chem. Abst., 71:30425a (1969).
Gavin, J. Org. Chem., 32, 2511 (1967).
Eilingsfeld, Ber., 97, 1232 (1964).
Chem. Abst., 57:7169h (1962).
Eilingsfeld, Agnew, Chem., 72, 836 (1960).
Chem. Abst., 61:6955b (1964).
Chem. Abst., 65:3791d (1966).
McKay, J. Med. Chem., 6, 587 (1963).
Short, J. Med. Chem., 6, 275 (1963).
Regan, J. Med. Chem., 10, 649 (1967).
Foye, J. Med. Chem., 6, 509 (1963).
Nakai, Bull. Chem. Soc., Japan, 43, 3528 (1970).
Campbell, J.A.C.S., 84, 3673 (1962).
Bredereck, Ber., 94, 2278 (1961).
Hankanen, Chem. Abst., 55:15406d (1961).
Ulrich, J. Org. Chem., 29, 2401 (1964).
Noller, Chemistry of Organic Compounds, (1956), p. 309.
Geluk, Jour. of Med. Chem., vol. 12, 1969, pp. 712–715.

*Primary Examiner*—Anton H. Sutto
*Assistant Examiner*—Michael Shippen
*Attorney, Agent, or Firm*—Martin B. Barancik; Roman Saliwanchik

[57] ABSTRACT

Novel compounds of FIG. 1, pharmaceutical compositions thereof, and systemic means of administration for anti-arrhythmic and diuretic uses are disclosed:

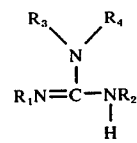

7 Claims, No Drawings

ADAMANTYL CONTAINING GUANIDINES

BRIEF DESCRIPTION OF THE INVENTION

It has been discovered that novel compounds of FIG. 1 are useful in the treatment of arrhythmic situations in mammals. Additionally, the compounds of this invention show diuretic activity. The compounds are formulated with pharmaceutical carriers into pharmaceutical compositions for oral and parenteral means of administration for anti-arrhythmic and diuretic uses.

DETAILED DESCRIPTION OF THE INVENTION

In accordance with this invention there are provided compounds hereafter referred to as Group A of FIG. 1

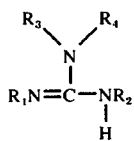

wherein $R_1$ and $R_2$ are the same or different and when $R_1$ and $R_2$ are the same they are adamantyl and when they are different, $R_1$ is adamantyl and $R_2$ is selected from the group consisting of hydrogen, alkyl of one to eight carbon atoms, inclusive, cycloalkyl of five to eight carbon atoms, inclusive, phenyl, phenalkyl where alkyl is one to three carbon atoms, inclusive, and monosubstituted phenyl wherein the substituent is selected from the group consisting of alkyl of one to three carbon atoms, inclusive, alkoxy of one to three carbon atoms, inclusive, halo, and trifluoromethyl.

$R_3$ and $R_4$ are the same or different and are selected from the group consisting of hydrogen and alkyl of one to eight carbon atoms, inclusive, cycloalkyl of five to eight carbon atoms, inclusive, and when taken together with the nitrogen atom to which they are attached form a saturated heterocyclic ring,

wherein Z is selected from the group consisting of methylene, NA where N is nitrogen and A is hydrogen or alkyl of one to three carbon atoms, inclusive, oxygen, and sulfur and when Z is methylene,

has from four to six carbon atoms, inclusive, and when Z is NA, oxygen or sulfur,

is respectively piperazino, N-alkylpiperazino, morpholino and thiomorpholino, and pharmaceutically acceptable acid addition salts thereof.

Another group of compounds, hereafter referred to as Group B, is $R_1$ and $R_2$ are defined as in Group A with the proviso that when $R_1$ and $R_2$ are different, and $R_1$ is adamantyl, $R_2$ is selected from the group consisting of hydrogen, alkyl of four to six carbon atoms, inclusive, cycloalkyl of five to seven carbon atoms, inclusive, and phenyl.

$R_3$ and $R_4$ are the saturated heterocyclics defined in Group A.

A further group of compounds, hereafter referred to as Group C is where $R_1$ and $R_2$ are the same or different and when the same are adamantyl and when different, $R_1$ is adamantyl and $R_2$ is cycloalkyl of five to seven atoms, inclusive.

$R_3$ and $R_4$ are defined as in Group B.

A still further group of compounds hereafter referred to as Group D, is where $R_1$ and $R_2$ are adamantyl and $R_3$ and $R_4$ are as defined in Group B.

Preferred compounds are N-1-adamantyl-N'-cyclohexyl-4-morpholinecarboxamidine and hydrochloride, N,N'-di-1-adamantyl-4-morpholinecarboxamidine and hydrochloride N,N'-di-2-adamantyl-4-morpholinecarboxamidine.

As employed in the above disclosure and throughout the specification, the term "halo" includes fluoro, chloro, bromo and iodo. The term "alkyl" includes methyl, ethyl, propyl, and isopropyl when limited to three carbon atoms and when limited to eight carbon atoms includes butyl, pentyl, hexyl, heptyl, octyl, and isomers thereof. The term "adamantyl" includes 1-adamantyl and 2-adamantyl. It should be noted that when $R_1$ and $R_2$ are the "same" and adamantyl, it is meant that both can be the one isomer, the two isomer, or $R_1$ can be the one isomer and $R_2$ can be the two isomer. "Pharmaceutically acceptable acid addition salts" include the hydrochloric, hydrobromic, hydriodic, nitric, sulfuric, phosphoric, acetic, lactic, citric, succinic, benzoic, salicylic, palmitic, cyclohexanesulfamic and the like.

The compounds of this invention can be prepared by methods known in the art. For example, an appropriately substituted carbodiimide (II) is reacted under suitable conditions with an appropriately substituted amine (III) to form a guanidine (IV).

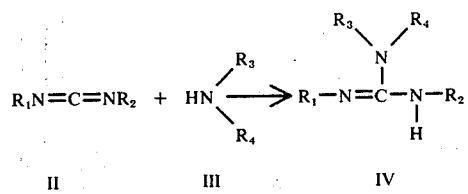

Reaction conditions for the above reaction and other synthetic procedures for preparing the guanidines are those known from the art. For example, various procedures for preparing carboniimides are outlined in F. Kurzer and K. Douraghi-Zadeh, Chem. Rev. 67, 107 (1967). Page 119 of the review article has a list of references for addition of amides to carbodiimides. An additional reference illustrating synthetic methods pertinent to this invention is German 1,192,453.

When $R_1$ and $R_2$ are different, guanidine tautomers are formed due to the mobility of the double bond. Consequently the compound exists in these tautomeric forms, that is

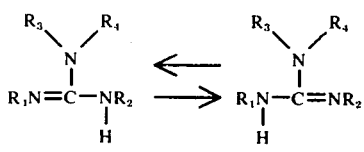

Compounds illustrative of the invention are the following:

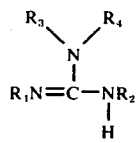

TABLE 1

| $R_1$ | $R_2$ | $R_3$ | $R_4$ |
|---|---|---|---|
| adamantyl | adamantyl | H | H |
| adamantyl | adamantyl | $C_2H_5$ | $iC_7H_{15}$ |
| adamantyl | adamantyl | H | cyclohexyl |
| adamantyl | adamantyl | $CH_3$ | cyclooctyl |
| adamantyl | adamantyl | piperidinyl | |
| adamantyl | adamantyl | pyrrolidinyl | |
| adamantyl | adamantyl | hexahydroazepinyl | |
| adamantyl | adamantyl | piperazinyl-NH | |
| adamantyl | adamantyl | N-ethylpiperazinyl | |
| adamantyl | adamantyl | morpholinyl | |

TABLE 1-continued

| $R_1$ | $R_2$ | $R_3$ | $R_4$ |
|---|---|---|---|
| adamantyl | adamantyl | thiomorpholinyl | |
| adamantyl | adamantyl | N-isopropylpiperazinyl | |
| adamantyl | cyclopentyl | pyrrolidinyl | |
| adamantyl | cyclohexyl | morpholinyl | |
| adamantyl | cycloheptyl | piperazinyl-NH | |
| adamantyl | cyclooctyl | N-ethylpiperazinyl | |
| adamantyl | cyclopentyl | H | $C_4H_9$ |
| adamantyl | cyclohexyl | $C_2H_5$ | $C_7H_{15}$ |
| adamantyl | cycloheptyl | $CH_3$ | cyclohexyl |
| adamantyl | cyclooctyl | H | cycloheptyl |
| adamantyl | | H | morpholinyl |
| adamantyl | | H | H |
| adamantyl | | H | $C_5H_{11}$ |
| adamantyl | | H | $iC_3H_7$ cyclohexyl |

TABLE 1-continued
| R₁ | R₂ | R₃ | R₄ |
|---|---|---|---|
|  | H | |  |
|  | CH₃ | |  |
|  | C₂H₅ | H | H |
|  | C₃H₇ | H | iC₈H₁₇ |
|  | tC₄H₉ | H |  |
|  | C₅H₁₁ | C₂H₅ |  |
|  | C₆H₁₃ | iC₃H₇ | tC₅H₁₁ |
|  | C₇H₁₅ | |  |
|  | C₈H₁₇ | |  |
|  |  | H | H |
|  |  | H | C₃H₇ |
|  |  | H |  |
|  |  | C₂H₅ | C₈H₁₇ |
|  |  | tC₄H₉ | C₅H₁₁ |
|  |  | iC₃H₇ |  |
|  |  | C₄H₉ |  |
|  |  |  |  |
|  |  | |  |
|  | 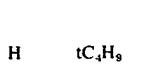 | |  |
| 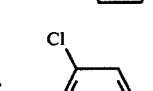 |  | |  |
|  | 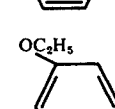 | H | tC₄H₉ |
|  |  | C₂H₅ | C₅H₁₁ |
|  |  | C₃H₇ |  |
|  |  |  |  |
|  |  | |  |
|  |  | |  |

TABLE 1-continued

| $R_1$ | $R_2$ | $R_3$ | $R_4$ |
|---|---|---|---|
| adamantyl | 4-(2-methyl-2-propyl)phenyl | H | $C_2H_{15}$ |
| adamantyl | 4-ethylphenyl (-$C_2H_4$-) | $C_3H_7$ | $C_7H_{15}$ |
| adamantyl | 4-(methylene)phenyl (-$CH_2$-) | | $CH_3$ (cyclohexyl) |

Following are specific examples of compounds within the invention and methods of preparing them. These examples are not intended to be limitations upon the broad scope of the invention, but merely illustrative of the scope.

EXAMPLE 1

N-1-Adamantyl-N'-cyclohexyl-4-morpholinecarboxamidine hydrochloride a. N-1-Adamantyl-N'-cyclohexylthiourea The thiourea is prepared by reacting 19.3 g. (0.1 mole) of 1-adamantyl isothiocyanate with 10 g. (0.1 mole) of cyclohexylamine in 250 ml. of ether at room temperature for 3 hrs. The thiourea which separates from solution is collected: 23.5 g., mp. 175–175.5. Evaporation of the ether filtrate to a small volume gives a second crop, 5.2 g., mp. 176–178. The combined yield is 28.7 g. (98.5 percent). A sample is recrystallized from alcohol and melts at 176°–177°.

Anal. Calc'd. for $C_{17}H_{27}N_2S$: C, 69.82; H, 9.65; N, 9.58. Found: C, 69.96; H, 9.81; N, 9.47.

b. Product

ROUTE 1

To a 0°–10° solution of 21 g. (0.21 mole) of phosgene in tetrahydrofuran is added 50 g. (0.17 mole) of N-1-adamantyl-N'-cyclohexylthiourea in one portion. The mixture is stirred at room temperature for 18 hrs. The solvent is removed under reduced pressure at bath temperature of 35°–40° and the residue is dissolved in 100 ml. of chloroform. This solution is added at 0°–10° to a solution of 50 g. (0.575 mole) of morpholine in 300 ml. of acetonitrile over 45 min. The reaction is stirred at 0°–10° for 30 minutes, then room temperature for 3.5 hrs., then reflux for 1.5 hrs. and finally left at room temperature for 16 hrs. The reaction is concentrated and residue dissolved in methylene chloride, diluted with ether and the organic layer is extracted with 20 percent sodium hydroxide solution. The organic layer is dried over potassium carbonate, evaporated and the residue diluted with toluene and concentrated to remove residual morpholine. The hydrochloride salt is prepared and recrystallized from acetonitrile-ether: 43.5 g., m.p. 232–234. Crop 2: 3.7 g., m.p. 222–224. The combined yield is 47.2 g. (73 percent). The analytical sample melts at 233–235.

Anal Calc'd. for $C_{21}H_{35}N_3O \cdot HCl$: C, 66.03; H, 9.50; N, 11.00; Cl, 9.28 Found: C, 65.91; H, 9.56; N, 10.68; Cl, 9.34

ROUTE 2

To a cold solution of 5 g. (0.05 mole) of phosgene in 110 ml. of tetrahydrofuran is added in one portion 11.7 g. (0.04 mole) of the thiourea. The reaction is stirred at room temperature for 18 hrs. The solvent is evaporated and the residue dissolved in about 30 ml. of chloroform. This solution is added dropwise over 15 min. to a solution of 5 g. of sodium hydroxide in 25 ml. of water at 0°–5°. The mixture is stirred for 10 min. more at 0°–5°. The chloroform layer is separated and combined with the chloroform extracts of the cold aqueous layer and dried over anhydrous potassium carbonate. The crude N-1-adamantyl-N-cyclohexylcarbodiimide is suspended in ether and the insoluble N-1-adamantyl-N'-cyclohexylurea filtered, and the filtrate evaporated to an oil. A mixture of the oil and 10 g. of morpholine in 10 ml. of tert-butyl alcohol is heated at reflux for 17 hrs. The reaction is diluted with toluene and concentrated. The hydrochloride salt is prepared and recrystallized from acetonitrile-ether: 2.6 g., m.p. 226–228. Crop 2. 2.1 g., m.p. 217–219. Combined yield is 4.7 g. (31 percent).

EXAMPLE 2

N,N'-di-1-Adamantyl-4-morpholinecarboxamidine and hydrochloride a. N-(1-Adamantyl)-4-morpholinethiocarboxamide The thiourea is prepared by reacting 5.0 g. (0.026 mole) of 1-adamantyl isothiocyanate with 2.5 g. (0.029 mole) of morpholine in 250 ml. of ether for ca. 1 hr. at room temperature. The solid which separates is collected and combined with additional compound from concentration of ether filtrate to a small volume: 6.65 g. (91 percent), m.p. 145–147. The analytical sample is recrystallized from ether, m.p. 148.

Anal. Calc'd. for $C_{15}H_{24}N_2OS$: C, 64.26; H, 8.63; N, 9.99 Found: C, 64.40; H, 8.79; N, 9.38 b. Product

To a suspension of 84 g. (0.3 mole) of N-(1-adamantyl)-4-morpholinethiocarboxamide is added a solution of 32.5 g. (0.325 mole) of phosgene in 650 ml. of tetrahydrofuran over 10 min. The reaction suspension is stirred at room temperature for 1.5 hrs. The solvent is evaporated in vacuo at a bath temperature of 40°–45°. The residue is dissolved in 750 ml. of methylene chloride and this solution is added over 45 min. to a solution of 45 g. (0.3 mole) of 1-adamantylamine in 300 ml. of N-methylmorpholine at 5°–10°. The reaction is stirred at 5°–10° for 1 hr. more, then room temperature for 17 hrs. The methylene chloride is distilled off over about 2 hrs. on the steam-bath. The reaction is concentrated in vacuo and the residue dissolved in methylene chloride, diluted with a large volume of ether. The organic layer is extracted several times with 10 percent hydrochloric acid. The hydrochloric salt precipitates. The precipitate is collected and then dissolved in about 300 ml. of warm water. The solution is filtered, cooled and basified with 20 percent sodium hydroxide solution to pH 13–14. The free base is collected and combined with the product obtained from basification of hydrochloric acid extracts. The N,N'-di-1-adamantyl-4-morpholinecarboxamidine is recrystallized from isopropanol: 38.3 g. (32 percent), m.p. 150–153. The analytical sample is recrystallized from isopropanol and melts at 151°–154°.

Anal. Calc'd. for $C_{25}H_{39}N_3O$: C, 75.52; H, 9.89; N, 10.57 Found: C, 75.40; H, 9.89; N, 10.24

The hydrochloride salt is recrystallized from methanolether; m.p. not definitive.

Anal. Calc'd. for $C_{25}H_{39}N_3O\cdot HCl$: C, 69.17; H, 9.29; N, 9.68; Cl, 8.17 Found: C, 69.12; H, 9.40; N, 9.68; Cl, 8.09

EXAMPLE 3

N,N'-di-2-Adamantyl-4-morpholinecarboxamidine a. N,N'-di-2-Adamantylthiourea

The 2-adamantylamine obtained from 5.0 g. (0.0266 mole) of 2-adamantylamine hydrochloride is reacted with 2.5 g. (0.014 mole) of 1,1'-thiocarbonyldiimidazole in 100 ml. of tetrahydrofuran for 20 hr. The solvent is evaporated and the residue partitioned between 5 percent hydrochloric acid and ether. The organic layer is washed with water, dried over potassium carbonate, evaporated and the residue is recrystallized from benzene-Skellysolve B: 3.65 g. (79 percent), m.p. 254–258.

Anal. Calc'd. for $C_{21}H_{32}N_2S$: C, 73.21; H, 9.36; N, 8.13 Found: C, 73.67; H, 9.70, N, 8.12 b. Product

A mixture of 3.45 g. (0.01 mole) of N,N'-di-2-adamantylthiourea, 3.15 g. (0.012 mole) of triphenylphosphine, 1.55 g. (0.01 mole) of carbon tetrachloride and 1.0 g. (0.01 mole) of triethylamine in 25 ml. of methylene chloride is stirred at 40°–45° for 2.5 hr. The solvent is evaporated and the residue which contained N,N'-di-2-adamantylcarbodiimide is reacted with 10 ml. of morpholine in 10 ml. of tert-butyl alcohol on a steam-bath for 16 hrs. The mixture is diluted with toluene and evaporated in vacuo to remove excess morpholine. The residue is partitioned between 10 percent hydrochloric acid and ether. Some solid insoluble in both phases is filtered off and discarded. The acid layer is combined with the water extracts of the ether layer. The acid layer is basified with 20 percent sodium hydroxide to pH 13–14 and nitrogen bubbled through the solution to remove ether. The solid which separated is collected, washed with water, airdried and recrystallized from isopropanol-water: 1.6 (40 percent), m.p. 123–124.

Anal. Calc'd. for $C_{25}H_{39}N_3O$: C, 75.52; H, 9.89; N, 10.57 Found: C, 75.35; H, 9.89; N, 10.40

The compositions of the present invention are presented for administration to humans and animals in unit dosage forms such as tablets, capsules, pills, powders, granules, sterile parenteral solutions or suspensions, oral solutions or suspensions and oil-in-water and water-in-oil emulsions and suppositories containing suitable quantities of the compound.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, powder packets, wafers, granules, cachets, teaspoonfuls, tablespoonfuls, dropperfuls, ampuls, vials, suppositories, segrated multiples of any of the foregoing, and other forms as herein described.

The administration of the compositions of the present invention to mammals bring about cardioregulatory action. Arrhythmia such as auricular fibrillation, ventricular fibrillation, paroxysmal atrial or ventricular tachycardia and the like, can be treated by this invention. Additionally, the compounds of the invention are useful as diuretics. As such they have the property of augmenting both urine volume and sodium excretion. This effect is of particular significance when the mammal suffering cardiac abnormalities, for example, arrhythmia, also has a buildup of bodily fluids.

For treating cardioregulatory problems such as arrhythmia an effective dosage of the particular compound is used. The particular dosage of the compound for treatment depends on the route of administration and the potency of the particular compound, as well as certain characteristics of the mammal being treated, such as weight and age. For treating arrhythmia in mammals orally or rectally, the dosage is from about 10 to about 1000 mg. per day in 1 to 4 equally divided doses. A preferred dosage range is from about 40 to about 400 mg. per day. Diuresis can be observed in the range of from about 1 to about 1000 mg. per day, preferably 10 to about 500 mg. per day. For treating arrhythmia in mammals parenterally, the dosage is from about 1 to about 500 mg. per day in 1 to 4 equally divided doses. A preferred dosage range is from about 10 to about 200 mg. per day. Diuresis can be observed in the range of from about 1 to about 500 mg. per day, preferably from about 10 to about 200 mg. parenterally.

EXAMPLE 4

A lot of 10,000 tablets, each containing 100 mg. of N-1-adamantyl-N'-cyclohexyl-4-morpholinecarboxamidine hydrochloride is prepared from the following types and amounts of ingredients:

| | |
|---|---|
| N-1-adamantyl-N'-cyclohexyl-4-morpholinecarboxamidine hydrochloride | 1000 gm. |
| Dicalcium phosphate | 1,000 gm. |
| Methylcellulose, U.S.P. (15 cps) | 60 gm. |
| Talc | 150 gm. |
| Corn starch | 200 gm. |
| Magnesium stearate | 10 gm. |

The compound and dicalcium phosphate are mixed well, granulated with 7.5 percent solution or methylcellulose in water, passed through a No. 8 screen and dried carefully. The dried granules are passed through a No. 12 screen, mixed thoroughly with the talc, starch and magnesium stearate, and compressed into tablets.

These tablets are useful in treating auricular fibrillation in man at a dose of 1 tablet 4 times a day.

EXAMPLE 5

One thousand two-piece hard-gelatin capsules, each containing 10 mg. of N,N'-di-1-adamantyl-4-morpholinecarboxamidine hydrochloride are prepared from the following types and amounts of ingredients:

| | |
|---|---|
| N,N'-di-1-adamantyl-4-morpholinecarboxamidine | 10 gm. |
| Dicalcium phosphate | 150 gm. |
| Talc | 15 gm. |
| Magnesium stearate | 1 gm. |

The ingredients are mixed well and filled into capsules of the proper size.

Capsules so prepared are useful in preventing paroxysmal tachycardia at a dose of one capsule every four hours.

EXAMPLE 6

One thousand tablets, each containing 300 mg. of N,N'-di-2-adamantyl-4-morpholinecarboxamidine are prepared from the following types and amounts of ingredients:

| | |
|---|---|
| N,N'-di-2-adamantyl-4-morpholinecarboxamidine | 300 gm. |
| Microcrystalline cellulose NF | 410 gm. |
| Starch | 100 gm. |
| Magnesium stearate powder | 4 gm. |

The ingredients are screened and blended together and pressed into 814 mg. tablets.

The tablets are useful in treating auricular fibrillations in man at a dose of one tablet four times a day.

EXAMPLE 7

One thousand tablets, each containing 125 mg. of N-1-adamantyl-N'-cyclohexyl-4-morpholinecarboxamidine hydrochloride are prepared from the following types and amounts of ingredients:

| | |
|---|---|
| N-1-adamantyl-N'-cyclohexyl-4-morpholinecarboxamidine hydrochloride | 125 gm. |
| Microcrystalline cellulose NF | 410 gm. |
| Starch | 100 gm. |
| Magnesium stearate powder | 3 gm. |

The ingredients are screened and blended together and pressed into 638 mg. tablets.

The tablets are useful in treating paroxysmal tachycardia and an increased fluid retention at a dose of four tablets per day.

EXAMPLE 8

A sterile preparation suitable for intramuscular injection and containing 25 mg. of N,N'-di-1-adamantyl-4-morpholinecarboxamidine hydrochloride in each milliliter is prepared from the following ingredients:

| | |
|---|---|
| N,N'-di-1-adamantyl-4-morpholinecarboxamidine hydrochloride | 25 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected four times daily for the treatment of auricular fibrillation.

EXAMPLE 9

A sterile preparation suitable for intramuscular injection and containing 25 mg. of N,N'-di-2-adamantyl-4-morpholinecarboxamidine in each milliliter is prepared from the following ingredients:

| | |
|---|---|
| N,N'-di-2-adamantyl-4-morpholinecarboxamidine | 25 gm. |
| Benzyl benzoate | 200 ml. |
| Methylparaben | 1.5 gm. |
| Propylparaben | 0.5 gm. |
| Cottonseed oil q.s. | 1,000 ml. |

Two milliliters of this sterile preparation is injected four times daily for treatment of paroxysmal tachycardia.

EXAMPLE 10

A sterile preparation suitable for intramuscular injection and containing 200 mg. of N-1-adamantyl-N'-cyclohexyl-4-morpholinecarboxamidine hydrochloride is prepared from the following ingredients:

| | |
|---|---|
| N-1-adamantyl-N'-cyclohexyl-4-morpholinecarboxamidine hydrochloride | 200 gm. |
| Benzyl benzoate | 200 ml. |
| Methylparaben | 1.5 gm. |
| Propylparaben | 0.5 gm. |
| Cottonseed oil q.s. | 1,000 ml. |

One milliliter of this sterile preparation is injected four times daily for treatment of auricular fibrillation and retention of bodily fluids.

EXAMPLE 11

Suitable quantities of each compound of Table I are compounded and used as in accordance with Examples 4–10. Similar results are obtained.

A rectal suppository can be employed to deliver the active compound where the mammal cannot be treated conveniently by means of other dosage forms, such as orally, as in the case of young children of debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

We claim:

1. A compound of the formula

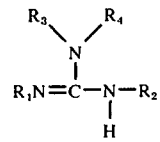

wherein $R_1$ and $R_2$ are the same or different and when $R_1$ and $R_2$ are the same they are adamantyl and when $R_1$ and $R_2$ are different, $R_1$ is adamantyl and $R_2$ is cycloalkyl of five to seven carbon atoms, inclusive;

$R_3$ and $R_4$ taken together with the nitrogen atom to which they are attached form a saturated heterocyclic ring $$\begin{pmatrix} Z \\ N \end{pmatrix}$$

wherein $$\begin{pmatrix} Z \\ N \end{pmatrix}$$

is pyrrolidino, piperidino, hexamethyleneimino, piperazino, N-alkylpiperazino wherein alkyl is one to three carbon atoms, inclusive, morpholino or thiomorpholino.

2. Compounds in accordance with claim 1 wherein $R_1$ and $R_2$ are adamantyl.

3. N-1-adamantyl-N'-cyclohexyl-4-morpholinecarboxamidine according to claim 1.

4. N-1-adamantyl-N'-cyclohexyl-4-morpholinecarboxamidine hydrochloride according to claim 1.

5. N,N'-di-1-adamantyl-4-morpholinecarboxamidine according to claim 1.

6. N,N-di-1-adamantyl-4-morpholinecarboxamidine hydrochloride according to claim 1.

7. N,N-di-2-adamantyl-4-morpholinecarboxamidine according to claim 1.

* * * * *